United States Patent [19]

Gracey et al.

[11] Patent Number: 4,996,232

[45] Date of Patent: Feb. 26, 1991

[54] REDUCING BACTERIAL CONTENT IN WATER

[75] Inventors: Michael Gracey, Wembley; Frank Hopkins, Glenfield; Jennifer Robinson, Floreat Park; Stephen Snow, Bargo, all of Australia

[73] Assignee: Cadbury Schweppes Proprietary Limited, Melbourne, Australia

[21] Appl. No.: 412,545

[22] Filed: Sep. 22, 1989

Related U.S. Application Data

[63] Continuation of Ser. No. 196,822, May 19, 1988, abandoned, which is a continuation of Ser. No. 920,672, Oct. 20, 1986, abandoned.

[30] Foreign Application Priority Data

Oct. 25, 1985 [AU] Australia ............................. PH3095
May 8, 1986 [AU] Australia ............................. PH5813

[51] Int. Cl.$^5$ ...................... A61K 31/34; A61K 31/19
[52] U.S. Cl. .................................. 514/474; 514/568; 514/574
[58] Field of Search ................... 514/568, 474, 574

[56] References Cited

U.S. PATENT DOCUMENTS

| | | | |
|---|---|---|---|
| 2,721,161 | 10/1955 | Maiese | 514/474 |
| 2,949,401 | 8/1960 | Wershaw | 514/474 |
| 3,789,008 | 1/1974 | Young | 514/568 |
| 4,229,430 | 10/1980 | Fahim et al. | 514/474 |
| 4,292,319 | 9/1981 | Tauber et al. | 514/568 |

FOREIGN PATENT DOCUMENTS

| | | |
|---|---|---|
| 147464 | 7/1985 | European Pat. Off. . |
| 0147464 A1 | 10/1985 | European Pat. Off. . |
| 1922653 | 11/1970 | Fed. Rep. of Germany ...... 514/474 |
| 3229097 | 2/1984 | Fed. Rep. of Germany ...... 424/303 |
| 58-121204 | 7/1983 | Japan .................................. 514/574 |
| 60-136506 | 7/1985 | Japan .................................. 514/474 |
| 1406540 | 9/1975 | United Kingdom . |

OTHER PUBLICATIONS

Sagarin, *Cosmetics Science & Technology*, pp. 1053, 1054, 1060 & 1067 (1957).

Linke, H. A. B. and Chang, C. A.: Z. Naturforschung (1976) 31 245–251, "Physiological Effects of Sucrose Substitutes and Artificial Sweeteners on Growth Pattern and Acid Production of Glucose-Grown Streptococcus Mutans Strains in Vitro".

*Primary Examiner*—Stanley J. Freidman
*Assistant Examiner*—Zohreh A. Fay
*Attorney, Agent, or Firm*—Larson and Taylor

[57] ABSTRACT

The invention provides dry compositions which when dissolved in water exhibit unexpectedly high antibacterial activity. The compositions comprise at least two of the following ingredients (a) to (d): (a) ascorbic acid and/or its salts (b) malic acid and/or tartaric acid and/or their salts (c) sodium saccharin and/or calcium saccharin (d) sodium benzoate and/or benzoic acid.

8 Claims, No Drawings

REDUCING BACTERIAL CONTENT IN WATER

This application is a continuation of application Ser. No. 07/196,822 filed May 19, 1988 which is a continuation of application Ser. No. 06/920,672 filed Oct. 20, 1986 now both abandoned.

This invention relates to compositions and processes for reducing the bacterial content of contaminated water.

In a general aspect the invention provides dry compositions which when dissolved in water exhibit unexpectedly high antibacterial activity. The compositions of the inventions preferably contain ascorbic acid, malic acid and/or tartaric acid, sodium saccharin and/or calcium saccharin and sodium benzoate and/or benzoic acid. The compositions of the invention include combinations of either the acids and/or salts of the abovementioned compounds. When dissolved in water the compositions of the invention preferably produce solutions of pH less than 5.0. For the treatment of contaminated water to make it potable, it is desirable to effect a reduction in *E. Coli* Log titre of at least $10^4$.

In many parts of the world, notably in developing countries in the tropics, provision of clean drinking water is a major problem and polluted water supplies are linked with the high prevalence of infectious diarrhea, particularly in children. A special problem needing attention is the preparation of clean, clear fluids for children with diarrhea, with or without signs of dehydration. Oral rehydration therapy is now widely used in developing countries for children with diarrhea and mild to moderate dehydration. If water used to prepare oral rehydration solutions is contaminated with faecal micro-organisms, bacterial multiplication can occur, particularly at tropical temperatures. Some bacteria, such as *Vibrio cholerae* and *Escherichia coli*, multiply more rapidly than others such as *Shigella flexneri*. Studies from Brazil and Central America show that bacteria will also multiply more rapidly in fluids which contain nitrogenous material as well as rehydration salts and water.

It is often very difficult to provide safe drinking water or oral rehydration fluids in places where childhood malnutrition and diarrhoea are prevalent. Metropolitan and town water supplies are often inadequately chlorinated or unchlorinated, often contaminated by sewage and other effluents in pipes or from surface waters, and boiling water is often inconvenient, and expensive. Simpler, inexpensive methods are needed to provide drinking water and oral rehydration fluids for children in developing countries.

Commercially available soft drink concentrates, which are known as cordials in Australia, are an important source of fluids for drinking by Australian children, particularly in summer when certain bacterial diarrhoeas are especially common in children.

In a previous investigation we found that non-carbonated, low-calorie cordials, when diluted according to manufacturers' instructions, has significant bacterial killing effects in the laboratory. Bacteria which were killed by the cordials included *Vibrio cholerae, Aeromonas hydrophila, Shigella sonnei, Salmonella typhimurium* and *Escherichia coli*. These bacteria are all well recognized causes of diarrhoea in humans. A preliminary report was published in Ann. Tropical Paediatrics (1985) 5 3-6.

Our previous work with cordials prompted us to investigate whether it would be possible to achieve this bactercidal effect with a powdered mixture which could be dissolved in water and then used as a drink. If this proved to be possible, this would provide a means of purifying water for drinking. Applications which would be appropriate for such a product include: prevention of water-borne diarrhoea in international travellers, expatriates living overseas, troops on active duty overseas or in remote areas, campers and hikers or for other people reliant on water supplies which are microbiologically suspect or sub-standard. The product would also be developed to provide clean fluids for treatment of patients with diarrhoea and dehydration by oral rehydration therapy and for refugees in camps, in disaster situations and in similar circumstances. The product could also be used to treat water for consumption by domestic and commercial animals and flocks.

In the course of this investigation we found that it was not possible to produce a suitable dry mixture simply by combining ingredients normally present in cordials. We unexpectedly found that certain components exhibited a synergistic effect when used in combination and also that certain mixtures were unsuitable for use due to chemical reactions that occurred when the dry powder was mixed with water. Further experimentation enabled us to overcome the latter difficulty.

The invention accordingly provides dry compositions capable of being dissolved in water which exhibit unexpectedly high antibacterial effects.

SUMMARY OF THE EXPERIMENTAL STUDIES

Experiments were conducted with substances, alone and in combination, which we considered possible candidates for antibacterial effects and could be used as a base for mixing with fluids for drinking.

The bacterium *Escherichia coli* was selected as the test micro-organism as our previous work had indicated that this organism was most resistant to the cordial It is also an organism that is used as a marker of water purity for Australian and World Health Organization standards, and is a major cause of infectious diarrhoea in adults and children around the world

The test system

A series of dilutions, containing between $10^9$ and $10^3$ colony forming units (CFU) of *Escherichia coli* was prepared. These were then added to the solutions and mixtures of substances under investigation. After incubation at room temperature, a sample (10ul) was then removed at the specified time, for the microbiological testing of the presence of bacteria. Results are given in Table 1. The rate of Kill of E. Coli is calculated by a linear regression of the power to which 10 must be raised to show cfu/mL(x) 'vs' time in minutes y (this is a statistical treatment of the microbiological results).

Time (minutes) $= x \cdot \log_{10}$ (cfu of E.Coli)—A (Zero error constant)

(X is time to reduce cfu by a factor of 10.)

TABLE 1

Solutions tested for ability to kill *E. Coli*
(quantities stated in grams/100 mL)

| Sucrose Colours, Flavours | Sodium Saccharin | Citric Acid | Tartaric Acid | Malic Acid | Ascorbic Acid | Sodium Benzoate | Time to reduce CPU *E. Coli* 10 fold. |
|---|---|---|---|---|---|---|---|
| 2.7 g | — | — | — | — | — | — | No Kill |
| — | 0.01 | — | — | — | — | — | No Kill |
| — | — | 0.38 | — | — | — | — | 62 mins |
| — | — | — | 0.30 | — | — | — | 41 mins |
| — | — | — | — | 0.27 | — | — | 59 mins |
| — | — | — | — | — | 0.015 | — | 105 mins |
| — | — | — | — | — | — | 0.11 | No Kill |
| — | 0.1 | 0.38 | — | — | — | — | 25 mins |
| — | 0.1 | — | 0.30 | — | — | — | 32 mins |
| — | 0.1 | — | — | 0.26 | — | — | 30 mins |
| — | — | — | — | 0.27 | 0.015 | — | 39 mins |
| — | — | — | — | 0.27 | 0.015 | 0.095 | 19 mins |
| — | — | 0.42 | — | — | — | 0.095 | 37 mins |
| — | — | — | — | 0.27 | — | 0.095 | 19 mins |
| — | — | — | 0.30 | — | — | 0.095 | 41 mins |
| — | — | — | — | 0.27 | — | 0.48 | 46 mins |
| — | — | — | — | 0.27 | — | 0.024 | 49 mins |
| — | — | — | — | — | 0.015 | 0.11 | 28 mins |
| — | — | 0.19 | 0.15 | 0.27 | — | 0.11 | 17 mins |
| — | — | 0.19 | 0.15 | 0.27 | 0.015 | 0.11 | 3.3 mins |
| 2.7 | 0.01 | 0.175 | — | 0.35 | 0.015 | 0.024 | 3.1 mins |
| 2.2 | — | — | 0.14 | 0.14 | 0.015 | 0.11 | 4.4 mins |

We have found that a mixture containing malic acid, ascorbic acid, sodium saccharin and sodium benzoate exhibits unexpectedly high antibacterial properties. Compositions containing citric acid and/or tartaric acid in addition to malic acid, ascorbic acid, sodium saccharin and sodium benzoate are even more effective.

In some cases difficulty was experienced in the use of these compositions because of a reaction of sodium benzoate with the food acids to form insoluble benzoic acid. We overcame this problem by coating the sodium benzoate with di-octyl sodium sulphosuccinate (DSS). DSS is a waxy solid which could be applied to the sodium benzoate, for example at a level of 2% by weight, in a 50% ethanol solution. This achieved complete solubilization.

The compositions of the invention are provided in palatable form for consumption by including one or more of colours, flavours, sweeteners (preferably Low Joule), bulking agent (sucrose, dextrose, polydextrose, lactose etc).

The following ingredients are employed in the ranges stated

| Powder Formulation to Deliver Beverage | Grams/100 ml of Made up |
|---|---|
| Ascorbic Acid | 0.001–1.0 |
| Malic Acid and/or Tartaric Acid | 0.01–1.0 |

*-continued*

| Powder Formulation to Deliver Beverage | Grams/100 ml of Made up |
|---|---|
| Sodium Saccharin and/or Calcium Saccharin | 0.000–0.1 |
| Sodium Benzoate (Benzoic acid) | 0.001–0.34 |

This also includes combinations of either the acids and/or salts of the above compounds in the ranges stated at pH's below 5.0.

The following combination of materials is effective in killing E. Coli:

| Ingredient | Weight/100 ml |
|---|---|
| Ascorbic acid | 0.015 grams |
| Malic acid | 0.27 grams |
| Citric acid | 0.19 grams |
| Tartaric acid | 0.15 grams |
| Sodium Benzoate | 0.11 grams |

This solution killed $10^6$ E. Coli/mL in 20 minutes.

This invention will be further illustrated by the following non-limiting examples.

| Example 1 Ingredient | Amount (expressed as %) |
|---|---|
| Sugar | 81.60 |
| Malic acid | 13.06 |
| Sodium benzoate | 1.80 |
| Ascorbic acid | 0.25 |
| Dioctyl sodium sulpho-succinate | 0.03 |
| Low-joule sweetener including sodium saccharin | |
| Colours | made up in combination 3.26 |
| Flavours | to |
| TOTAL | 100.00 |

This mixture is to be made up with water in the following way for drinking: 6.127 of mixture to 100 mls of water

| Example 2 | % |
|---|---|
| Lactose or Polydextrose | 86.89 |
| Tartaric Acid | 10.00 |
| Sodium Benzoate | 0.01 |
| Low Joule Sweetener(s) including sodium saccharin | |
| Colours/Flavours | 3.0 |
| TOTAL | 100.00 |

5 grams of mixture/100mL of water for drinking.

| Example 3 | | |
|---|---|---|
| Malic Acid | 79.9 | 0.1 |
| Ascorbic Acid | | 20.0 |

0.5 grams of mixture/100mL of water for drinking.

It will be clearly understood that the invention in its general aspects is not limited to the specific details referred to hereinabove.

We claim:

1. A dry composition useful for its antibacterial activity when dissolved in water, said composition consisting essentially of the following ingredients in amounts that will deliver the specified number of grams per 100 ml when dissolved in water:

| (a) Ascorbic acid or pharmaceutically-acceptable salts thereof | 0.001–1.0 |
|---|---|
| (b) Malic acid or pharmaceutically acceptable salts thereof | 0.01–1.0 |
| (c) At least one of sodium saccharin and calcium saccharin | up to 0.1 |
| (d) Sodium benzoate or benzoic acid | 0.001–0.34 |

2. A composition according to claim 1, further comprising at least one compound selected from the group consisting of citric acid and tartaric acid.

3. A composition according to claim 1, wherein ingredient (d) comprises sodium benzoate which has been coated with di-octyl sodium sulphosuccinate in an amount sufficient to promote solution of sparingly soluble benzoic acid which is formed at the sodium benzoate crystal/solution interface during dissolving of the dry composition in water as a result of action of other organic acids in solution.

4. A dry composition useful for its antibacterial activity when dissolved in water, said composition consisting essentially of the following ingredients in the specified relative proportions expressed in parts by weight:

| sodium saccharin | 10 |
|---|---|
| citric acid | 175 |
| malic acid | 35 |
| ascorbic acid | 15 |
| sodium benzoate | 24 |

5. A dry composition useful for its antibacterial activity when dissolved in water, said composition consisting essentially of the following ingredients in the specified relative proportions expressed in parts by weight:

| citric acid | 19 |
|---|---|
| tartaric acid | 15 |
| malic acid | 27 |
| ascorbic acid | 15 |
| sodium benzoate | 110 |

6. A dry composition useful for its antibacterial activity when dissolved in water, said composition consisting essentially of the following ingredients in the specified relative proportions expressed in parts by weight:

| tartaric acid | 140 |
|---|---|
| malic acid | 140 |
| ascorbic acid | 15 |
| sodium benzoate | 110 |

7. A method for reducing the bacterial content of contaminated water which comprises dissolving an antibacterial effective amount of a composition according to claim 1 in the said contaminated water.

8. A dry composition according to claim 1 comprising at least one further ingredient selected from the group consisting of coloring, flavoring, sweetening and bulking agents.

* * * * *